(12) United States Patent
Islava

(10) Patent No.: US 10,517,751 B2
(45) Date of Patent: Dec. 31, 2019

(54) VACUUM SPLINT APPARATUS FOR ACCOMMODATING THE CHIN OF A PATIENT AND METHOD FOR USING THE SAME

(71) Applicant: Steve Islava, Newport Beach, CA (US)

(72) Inventor: Steve Islava, Newport Beach, CA (US)

(*) Notice: Subject to any disclaimer, the term of this patent is extended or adjusted under 35 U.S.C. 154(b) by 367 days.

(21) Appl. No.: 15/496,881

(22) Filed: Apr. 25, 2017

(65) Prior Publication Data

US 2017/0224521 A1    Aug. 10, 2017

Related U.S. Application Data

(63) Continuation-in-part of application No. 15/061,820, filed on Mar. 4, 2016, now Pat. No. 10,357,393, and a continuation-in-part of application No. 14/962,862, filed on Dec. 8, 2015, now Pat. No. 10,245,174.

(51) Int. Cl.
*A61F 5/055* (2006.01)
*A61F 5/058* (2006.01)
*A61F 5/37* (2006.01)

(52) U.S. Cl.
CPC .......... *A61F 5/05883* (2013.01); *A61F 5/055* (2013.01); *A61F 5/05816* (2013.01); *A61F 5/05833* (2013.01); *A61F 5/3707* (2013.01); *A61H 2201/1604* (2013.01)

(58) Field of Classification Search
CPC ...... A61F 5/055; A61F 5/05883; A61F 5/012; A61F 5/05816; A61F 5/3707; A61F 2007/0011; A61F 5/05; A61F 5/058; A61F 2250/0004; A61F 2007/0009; A61F 2007/001; A61F 2250/0003; A61F 5/024; A61F 5/048; A61F 13/12; A61F 13/128; A61H 9/0078

See application file for complete search history.

(56) References Cited

U.S. PATENT DOCUMENTS

| D261,430 S | 10/1981 | Baturin | |
| 5,029,577 A * | 7/1991 | Sarkozi | A61F 5/055 602/18 |
| 6,918,393 B2 | 7/2005 | Rugfelt | |
| 9,289,320 B2 * | 3/2016 | Hollern | A61F 5/055 |
| 2003/0158015 A1 * | 8/2003 | Watson | A63B 21/028 482/10 |
| 2004/0082891 A1 * | 4/2004 | Daugherty | A61F 5/05833 602/5 |

(Continued)

*Primary Examiner* — Ophelia A Hawthorne
(74) *Attorney, Agent, or Firm* — Marcus C. Dawes; Daniel L. Dawes

(57) ABSTRACT

A particle filled neck brace is used for immobilizing the neck and chin of a patient and includes a vacuum pump disposed on the neck brace, which pump is communicated to the interior of the neck brace. After the neck brace is secured around the neck and chin of the patient, the vacuum pump is manipulated to remove air from the neck brace to form a rigid mold about the patient's neck and chin. The vacuum pump has a one way directional valve so that the neck brace remains in a rigid configuration for as long as the neck brace is applied to the patient. The neck brace also specifically forms a rigid mold over the patient's chin so as to immobilize the patient as well as to provide a comfortable fit without inducing further distracting the patient or restricting the patient's venous return blood flow.

18 Claims, 19 Drawing Sheets

(56) References Cited

U.S. PATENT DOCUMENTS

2006/0155227 A1    7/2006  Daugherty
2007/0066922 A1*  3/2007  Farley .................... A61F 5/012
                                                              602/18
2007/0116935 A1    5/2007  Renberg
2012/0277644 A1  11/2012  Williams

* cited by examiner

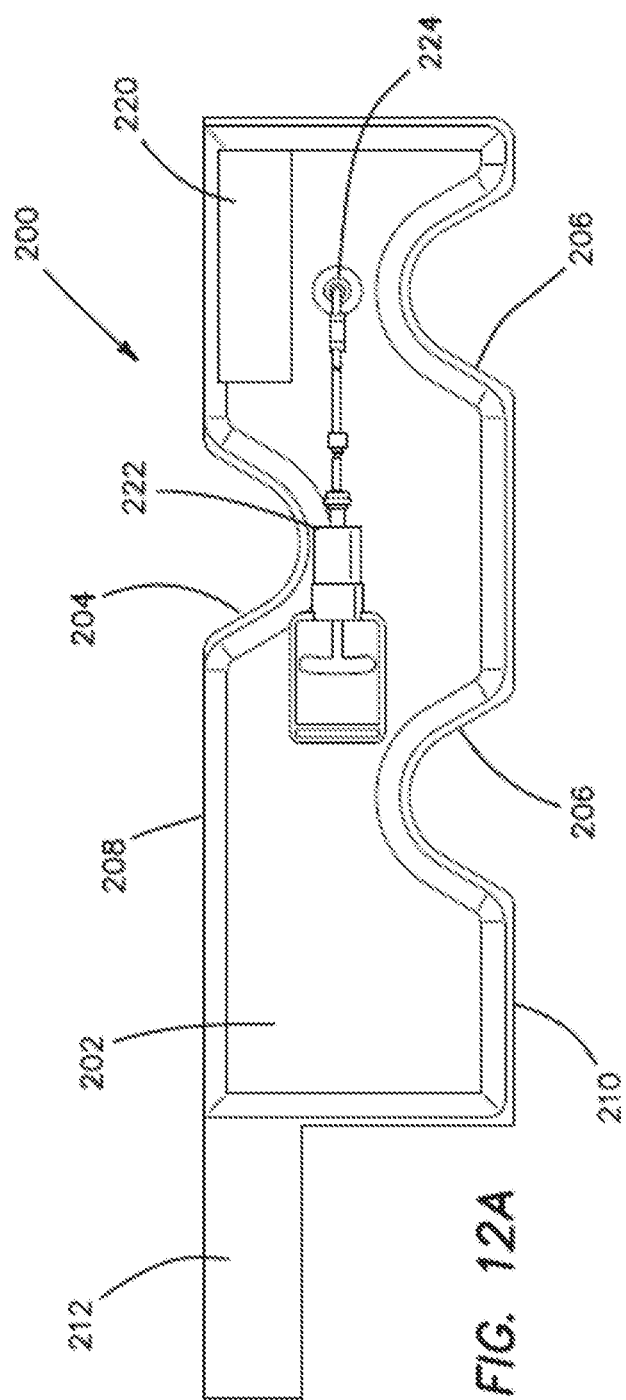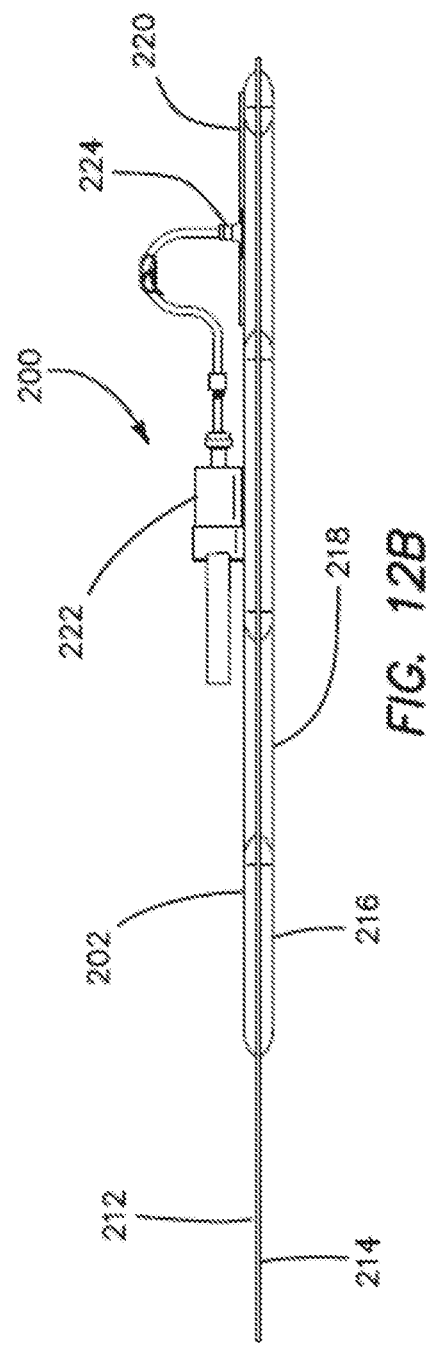

VACUUM SPLINT APPARATUS FOR ACCOMMODATING THE CHIN OF A PATIENT AND METHOD FOR USING THE SAME

RELATED APPLICATIONS

The present application is a Continuation in Part application of U.S. application Ser. No. 15/061,820, filed on Mar. 4, 2016, which in turn is a Continuation in Part application of U.S. application Ser. No. 14/962,862, filed on Dec. 8, 2015, which are incorporated herein by reference and to which priority is claimed pursuant to 35 USC 120.

BACKGROUND

Field of the Technology

The invention relates to the field of pneumatic splints, specifically a vacuum operated splint for immobilizing the neck of a patient.

Description of the Prior Art

Medical splints and other immobilizers have long been used to immobilize or otherwise restrict the physical movement of a region or limb of an injured patient. Many traditional splints are made from cardboard, plastic, padded board, or fiberglass and may either be generic in shape or specifically formed to fit a specified limb or body part of the patient. Typically, the splint is placed under the injured portion of the patient and is then tightened to straighten and/or immobilize the body part to prevent further relative movement of the body part and thus prevent further injury and allow the patient an opportunity to heal. Some splints include vacuum or pneumatic pumps which inflate the splint with air until a tight hold is achieved around the injured portion of the patient.

A type of splint that is made to fit a specific body part is the neck brace, which is specifically shaped and formed to fit about the neck of the patients while also accommodating their shoulders and face. The most basic neck brace is the soft collar which consists of a section of soft foam that wraps around the neck of the patient and is then held in place with a temporary means of coupling such as Velcro and the like. Other neck braces comprise a semi-rigid plastic frame with a soft inner foam padding which is likewise placed around the injured patient's neck and then held in place with interlocking straps or a sliding or telescopic track element.

A problem with many neck braces, however, is that many of them must be adjusted before being applied to the patient's neck. Therefore before the patient's neck can be immobilized, the person applying the brace must first assess the patient and then manipulate the brace in order to ensure that an appropriate fit is achieved when placed around the patient's neck. This can be critical in emergency situations when an EMT or other medical responder first arrives at an accident scene when every second counts. Inflatable neck braces do not require any pre-adjustment according to size however they do require the coupling and activation of an external pump device before the patient may be sufficiently immobilized. Again, in emergency situations when time and physical access to the injured patient may be limited, such an inflatable neck brace could prove to be more detrimental to the treatment of the patient than other braces.

What is needed therefore is a neck brace which can be easily and quickly applied to an injured patient of any size, which does not require any external pumps for operation and which also properly immobilizes the neck of the patient and prevents for further injury.

BRIEF SUMMARY

The current invention provides for a customizable neck brace which includes a front panel and a back panel, where an internal volume is defined between the front panel and the back panel. The neck brace also includes a strip that is attached to its front panel, the strip having a first coupling portion disposed on its surface. The neck brace further includes a second coupling portion disposed on its front panel and a plurality of loosely compressible particles disposed within its internal volume. Removably attached to the front panel of the neck brace is a detachable pump assembly. Both the front and back panel of the neck brace further include a neck contour that is defined into its respective surfaces.

In one embodiment, the detachable pump assembly includes a chamber, a handle attached to a first end of the chamber, and a plunger disposed within an internal portion of the chamber. The pump assembly further includes a nozzle disposed within a second end of the chamber and a collar which is in turn attached to the nozzle. The pump assembly additionally inlcudes a female luer lug which is coupled to the nozzle via a flexible connecting line.

In a related embodiment, the detachable pump assembly further includes a vacuum line that is attached to an input valve that is disposed in the front panel. The opposing end of the vacuum line in turn includes a male luer lock. Additionally, the pump assembly may include a hose clamp that is coupled to the vacuum line.

In yet another embodiment, the front panel of the neck brace also includes an input valve that is fluidly communicated to the internal volume. Relatedly, the input valve may also include a filter screen that is disposed between the internal volume an internal portion of the input valve.

In a separate embodiment, the neck brace further includes a supplemental coupling portion disposed on the back panel.

In yet another embodiment, the neck brace includes a plurality of shoulder contours that are defined in both the front panel and the back panel.

In a separate embodiment, the front panel and the back panel of the neck brace cooperate to form a patient-specific mold around the neck of and chin of a patient after the detachable pump assembly has been actuated.

The invention further provides a method for forming an immobilizing patient-specific mold wherein the method includes wrapping a neck brace around the neck and chin of a patient, the neck brace having a front panel and a back panel and having an interior volume defined therebetween which is filled with a plurality of compressible particles. The method further includes actuating a detachable pump assembly that is removably coupled to the front panel of the neck brace and then removing air from the internal volume of the neck brace to compress the neck brace and forming a unique rigid mold about the neck and chin of the patient.

In one embodiment, the method step of actuating the detachable pump assembly includes connecting the pump unit to a vacuum line which is itself communicated to the internal volume of the neck brace. A plunger disposed within a chamber of the pump unit is then actuated which then removes air from the internal volume of the neck brace through the vacuum line.

In one particular embodiment, removing air from the internal volume of the neck brace through the vacuum line also involves preventing the plurality of compressible particles within the internal volume from escaping and entering the vacuum line by means of a filter screen.

In another embodiment, attaching the pump unit to a vacuum line which is communicated to the internal volume of the neck brace includes connecting a female luer lug that is disposed on the pump unit to a male luer lock that is disposed on the vacuum line.

In yet another embodiment, the method step of forming a unique rigid mold about the neck and chin of the patient includes accommodating the chin of the patient in an immobilized position within the unique rigid mold.

In a related embodiment, the step of forming a unique rigid mold about the neck and chin of the patient further includes preventing restriction of the venous blood flow return of the patient.

Finally, the current invention provides a method for preventing the distraction of the neck of a patient when immobilizing the patient's neck. Here, the method includes disposing a neck brace about the neck of a patient while the neck of the patient is in an injured position. Next, the neck brace is actuated to form a unique rigid mold about the injured region of the patient's neck, the formed unique rigid mold being configured to maintain the neck of the patient within its original injured position for the duration that the neck brace is disposed about the neck of the patient.

In one particular embodiment, actuating the neck brace to form a unique rigid mold about the injured region of the patient's neck involves compressing the neck brace to fit the specific contours of the patient's neck and chin.

In another embodiment, the method also includes inflating the neck brace in order to remove the neck brace from the neck of the patient.

In another embodiment, the method step of disposing the neck brace about the neck of a patient while the neck of the patient is in an injured position includes attaching either a first coupling portion or a supplemental coupling portion located on a first surface of the neck brace to a second coupling portion located on a second surface of the neck brace.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 12A is a top down perspective view of an alternative embodiment the neck brace comprising a detachable pump assembly.

FIG. 12B is a frontal perspective view of the neck brace seen in FIG. 12A.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
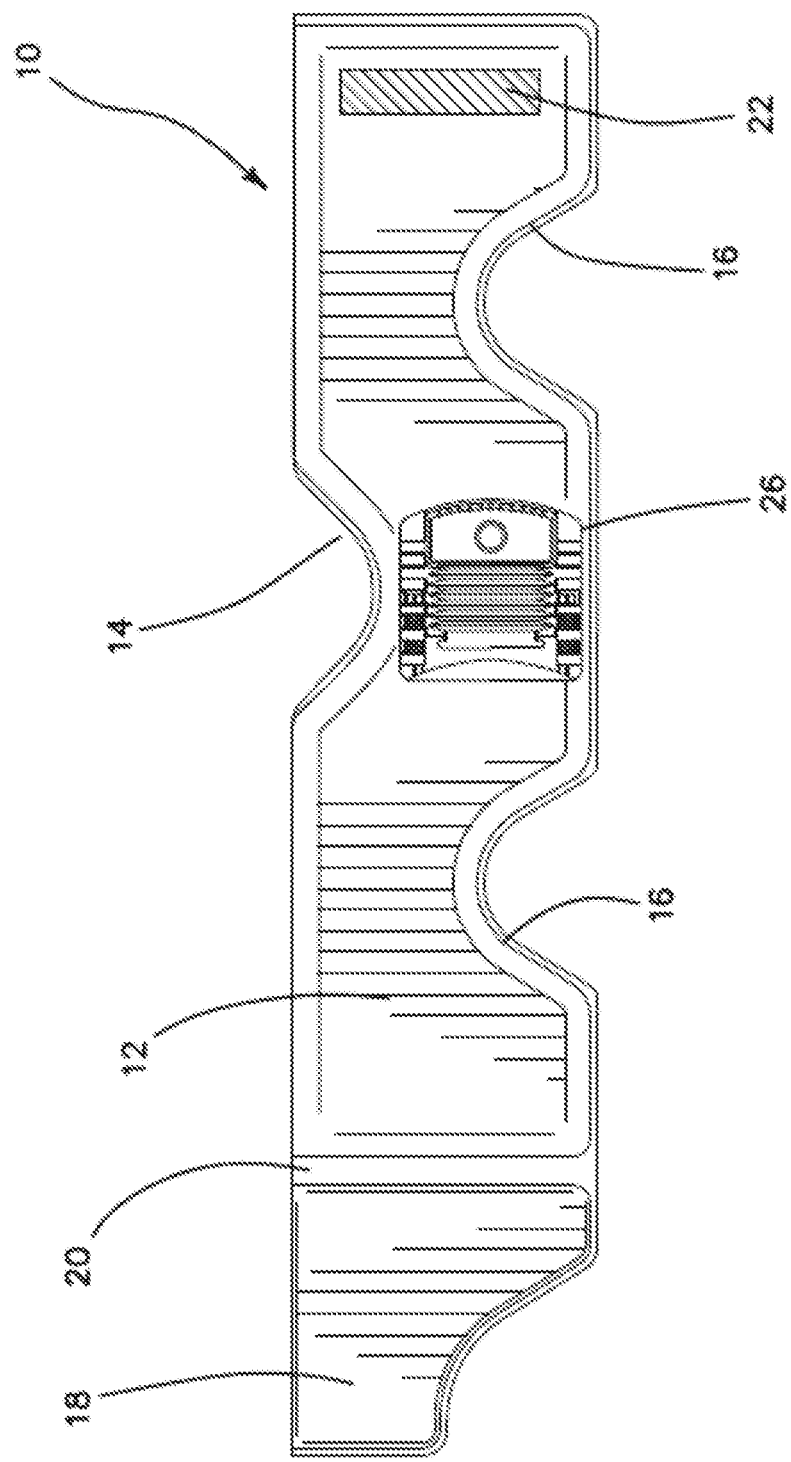
FIG. 1 is a frontal plan view of the neck brace of the illustrated embodiments of the current invention.
Figure 2:
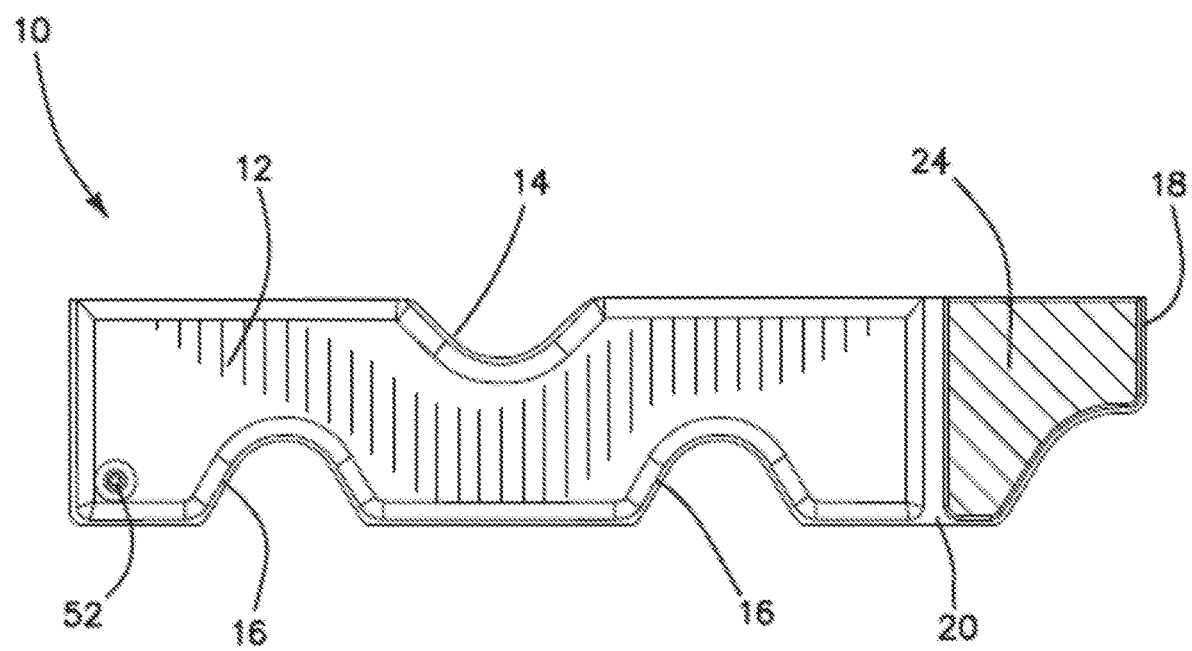
FIG. 2 is a rear plan view of the neck brace seen in FIG. 1.

Greater detail of the illustrated embodiments of the current invention may be had by turning to FIGS. 1 and 2 which shows the current neck brace denoted generally by reference numeral 10. FIG. 1 shows a frontal view of the brace 10 which comprises of a body 12 that is substantially rectangular in shape. The body 12 itself comprises a neck cutout 14 and a plurality of shoulder cutouts 16. The neck cutout 14 and shoulder cutouts 16 are sized and defined in the body 12 at the appropriate locations so that when the neck brace 10 is applied to a patient's neck region, the neck cutout 14 appropriately accommodates the jaw and head of the patient while the shoulder cutouts 16 accommodate the shoulders and chest region of the patient as is known in the art. The body 12 itself is comprised of soft vinyl or other flexible material and is filled with a plurality of foam micro beads known in the art.

The body 12 further comprises a coupling portion 18 joined to the remainder of the body 12 via a flexible region 20. Like the main part of the body 12, the coupling portion 18 is also filled with a plurality of foam micro beads. The flexible region 20 however does not have any micro beads. The coupling portion 18 is used to join the opposing ends of the body 12 together when the neck brace 10 is placed around the neck of the injured patient. Specifically, as seen in the rear view of the neck brace 10 in FIG. 2, the back surface of the coupling portion 18 comprises a hook and latch fabric pad 24 so that when the neck brace 10 is placed on the patient, the coupling portion 18 is brought around to the opposing end of the front of the body 12 where an opposing hook and latch fabric pad 22 is disposed. The medical professional secures the neck brace 10 in place by aligning the hook and latch fabric pad 24 on the back surface with the opposing pad 22 on the front surface and adhering the pad 24 and opposing pad 22 together. The pads 24, 22 are brought together relative to one another according to the width or circumference of the patient's neck and shoulder region. To release the neck brace 10, the coupling portion 18 is pulled away from the patient which in turn pulls the pad 24 away from the opposing pad 22 of hook and latch fabric thus releasing the ends of the body 12 from each other. With the opposing ends of the body 12 separated, the neck brace 10 may be removed from the neck and shoulder region of the patient.

Figure 3:
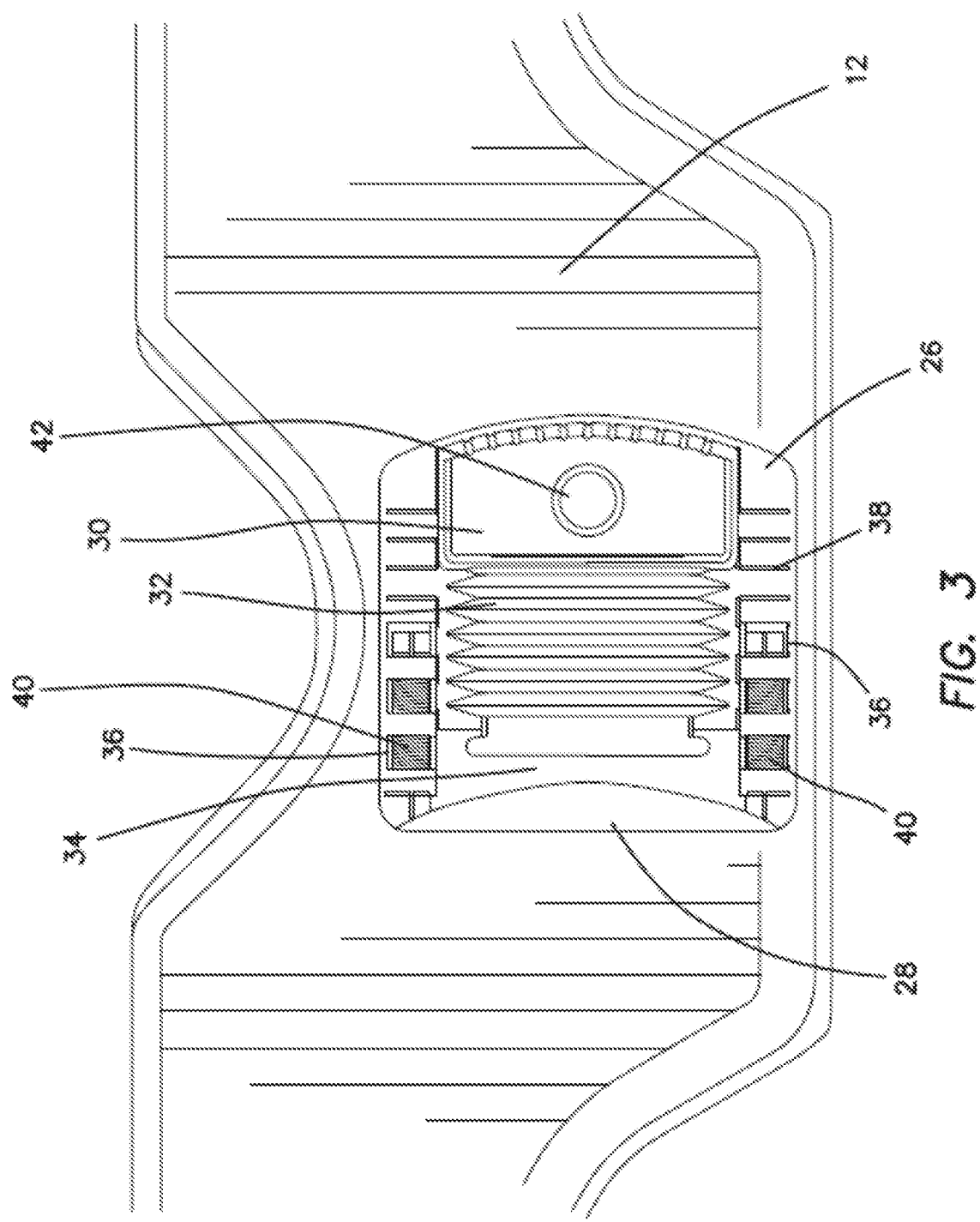
FIG. 3 is a magnified view of a hand pump disposed on a body portion of the neck brace seen in FIG. 1.

Also seen in FIG. 1 is a vacuum hand pump 26 which is disposed on the front surface of the body 12. While the vacuum hand pump 26 is shown as being disposed substantially beneath the neck cutout 14, it is to be expressly understood that the vacuum hand pump 26 may located anywhere on the body 12 of the neck brace 10 without changing the overall function or scope of the claimed invention. Greater detail of the vacuum hand pump 26 may be seen in the magnified views of FIGS. 3 and 4. The vacuum hand pump 26 comprises a housing 30 with a frame 28 disposed around it. Coupled to the housing 30 is a bellows 32 which may be compressed against the housing 30 as detailed further below. Coupled to a distal end of the bellows 32 is a plunger 34. The plunger 34 is sufficiently sized and shaped so that a medical professional may easily grip and press the plunger 34 with his or her fingers. The plunger 34 itself comprises a shuttle 36 disposed on either lateral side of the plunger 34. Each shuttle 36 is disposed in a corresponding track 38 formed within the lateral sides of the frame 28. Also disposed in each track 38 is a tension spring 40 which is coupled to the frame 28 at one end and coupled to the shuttle 36 at the opposing end.

Figure 6:
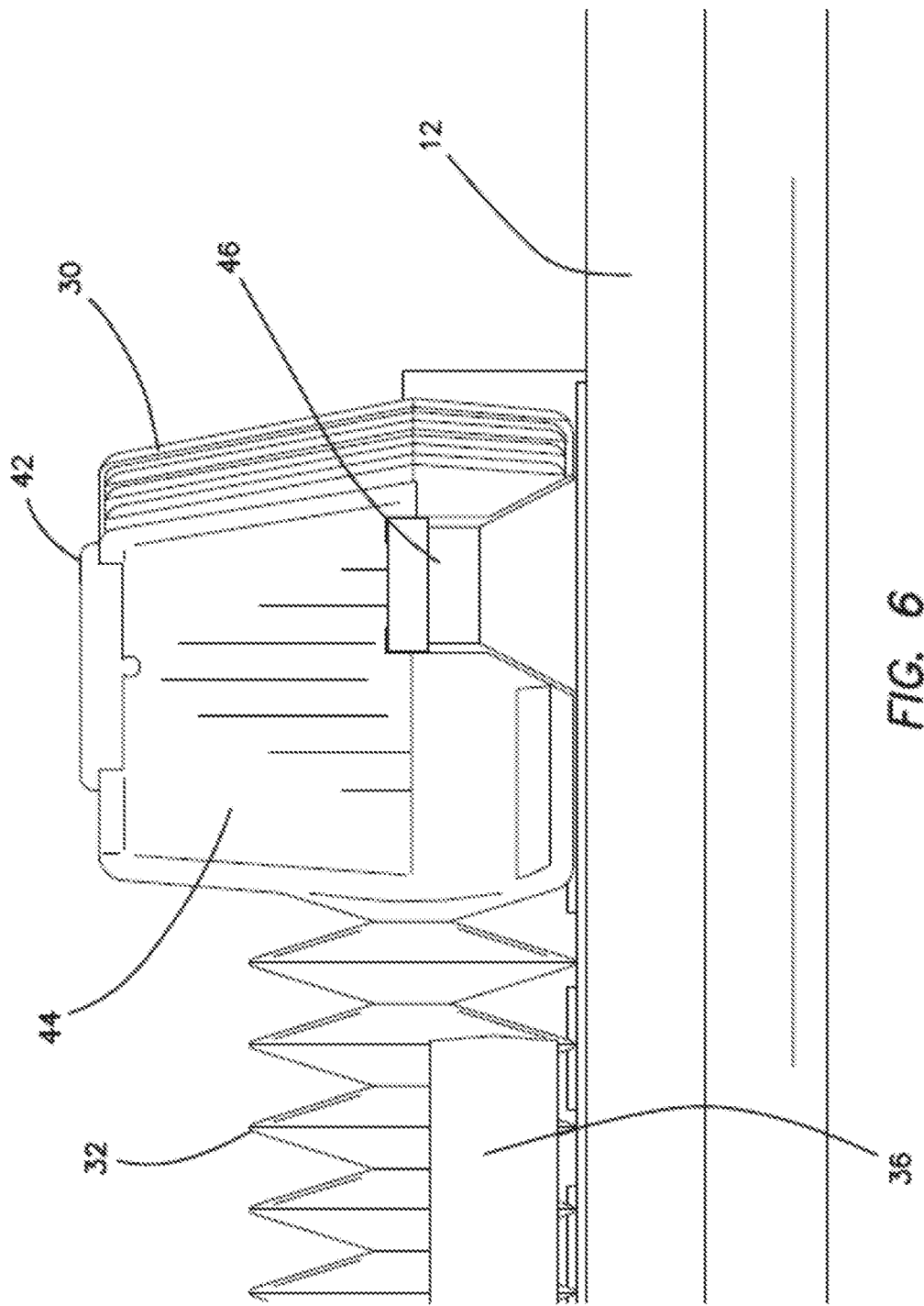
FIG. 6 is a magnified cross sectional view of the vacuum hand pump seen in FIG. 3, including the housing portion of the hand pump.
Figure 9:
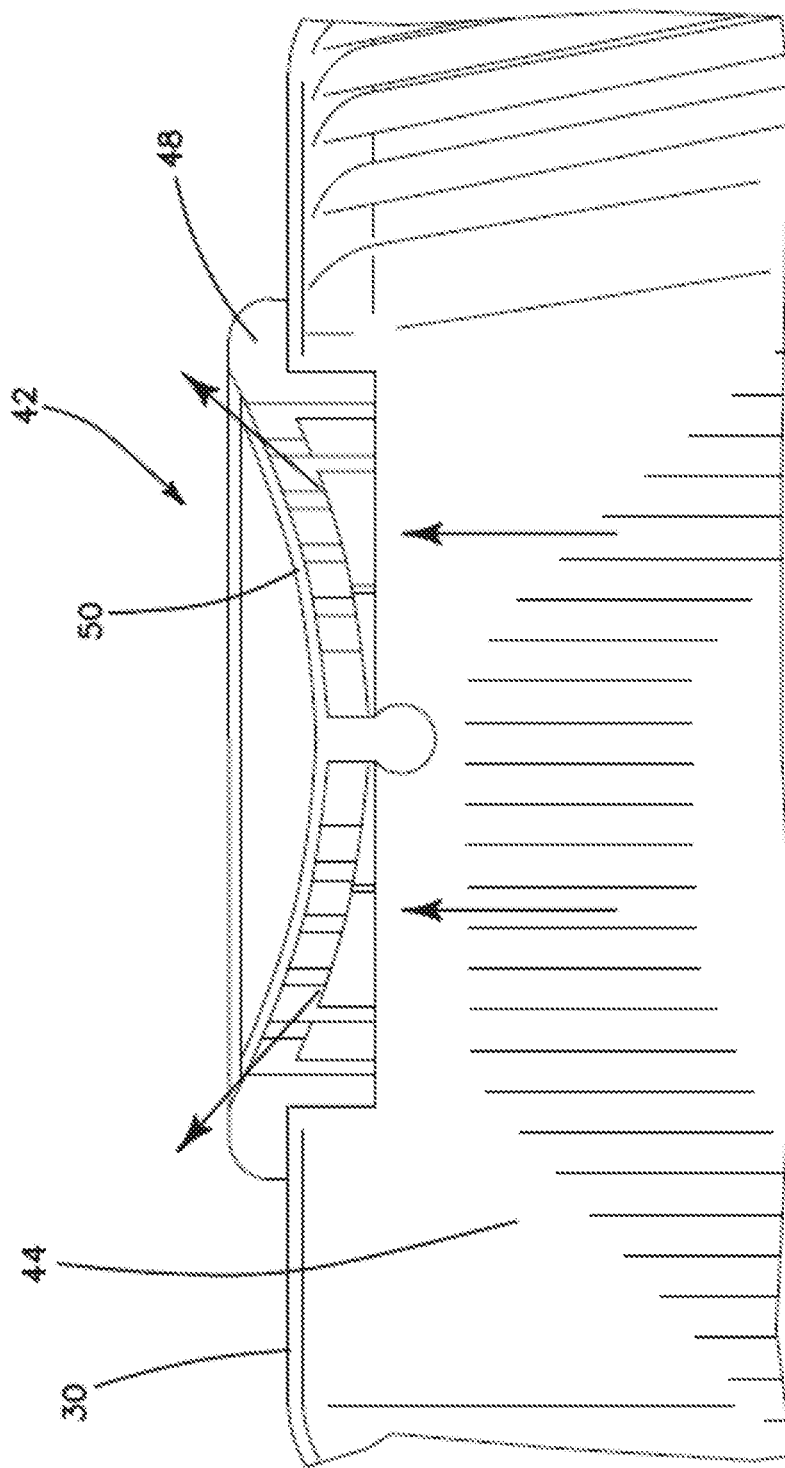
FIG. 9 is a magnified cross sectional view of a one-way directional valve disposed in a surface of the housing seen in FIG. 6.

Greater detail of the housing 30 and the components contained therein may be seen in FIG. 6. The housing 30 comprises an internal chamber 44 for passing a volume of air from the body 12 of the neck brace 10 to the outside environment. Also disposed within the housing 30 is a body valve 46 which is fluidly coupled to an internal volume of the body 12. As is known in the art, the body valve 46 is a one-way directional valve which allows for air to flow in substantially only one direction, namely from the body 12 to the internal chamber 44 of the housing 30. Disposed in the top surface of the housing 30 is a housing valve 42, which like the body valve 46, is a one-way directional valve which allows air to flow in only one direction from the internal chamber 44 of the housing 30 to the ambient environment. Detail of the housing valve 42 may been seen in FIG. 9 which shows the housing valve 42 comprising a substantially annular or ring shaped valve seat 48 and a flexible diaphragm 50. As seen in the cross sectional view of FIG. 9, the diaphragm 50 is disposed within the center of the valve seat 48 with outer circumference of the diaphragm 50 resting on an inner radius of the valve seat 48.

Figure 4:
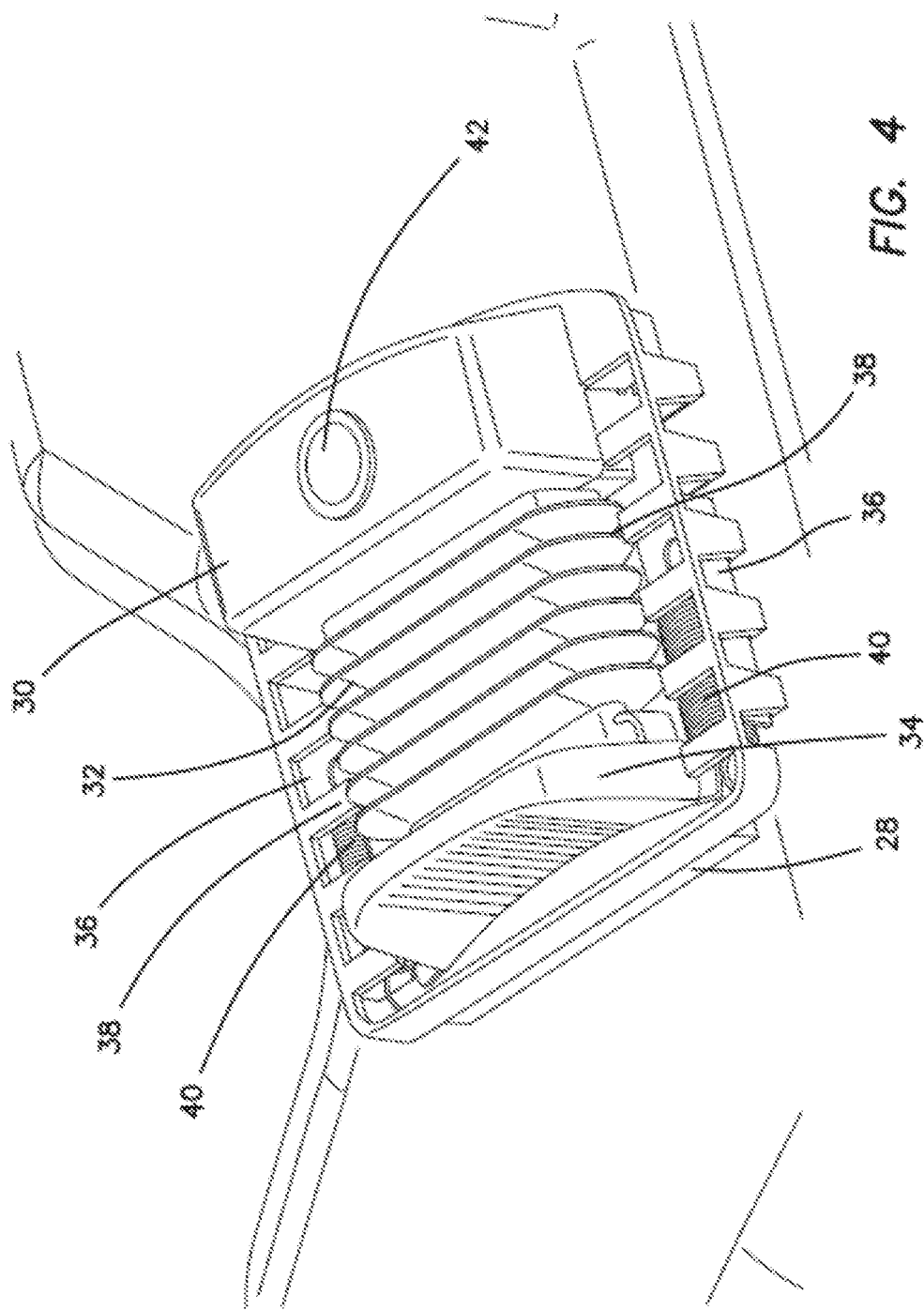
FIG. 4 is a perspective view of the vacuum hand pump disposed on the neck brace when the hand pump is in an expanded configuration.
Figure 5:
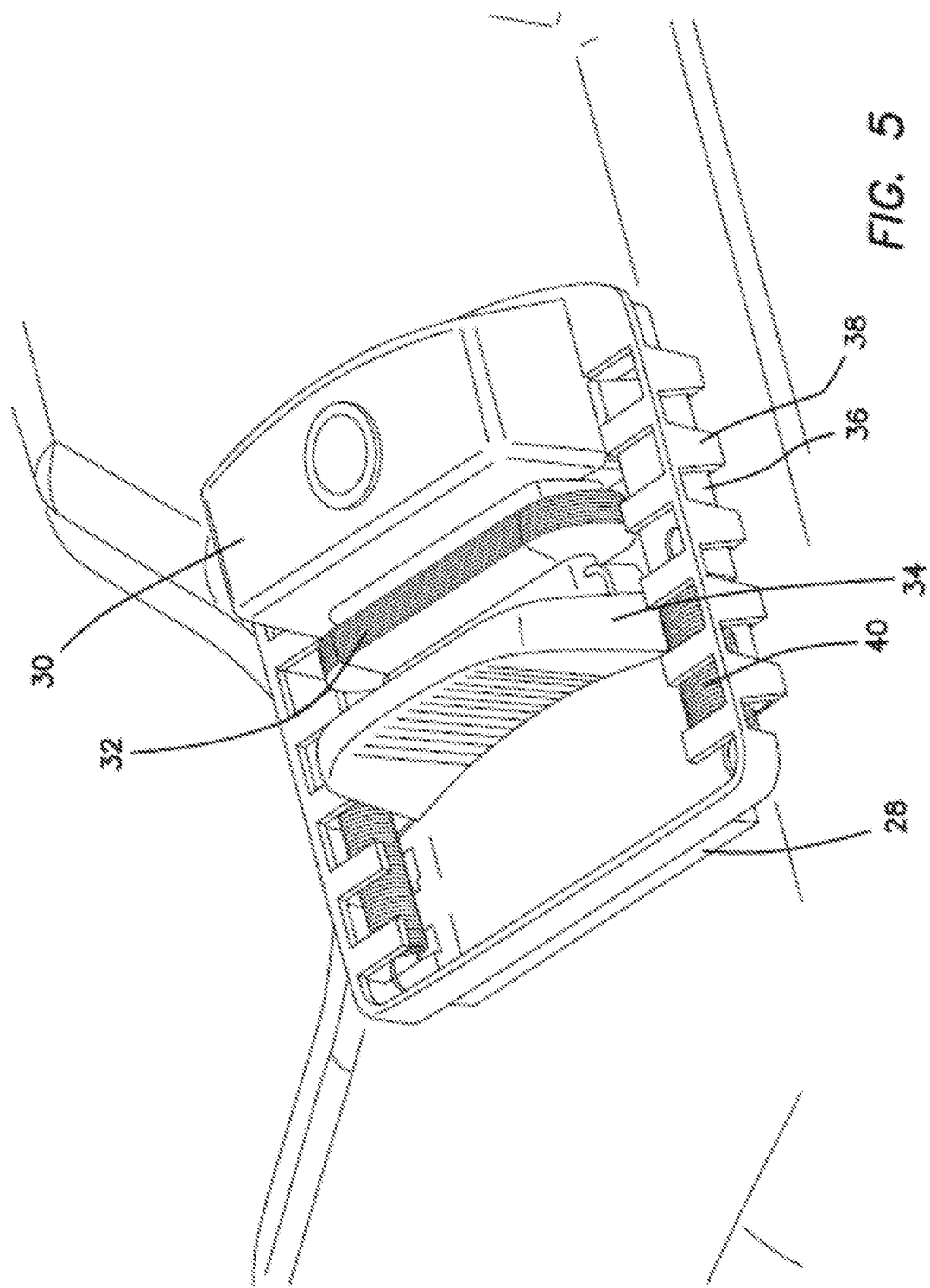
FIG. 5 is a perspective view of the vacuum hand pump disposed on the neck brace when the hand pump is in a compressed configuration.
Figure 7:
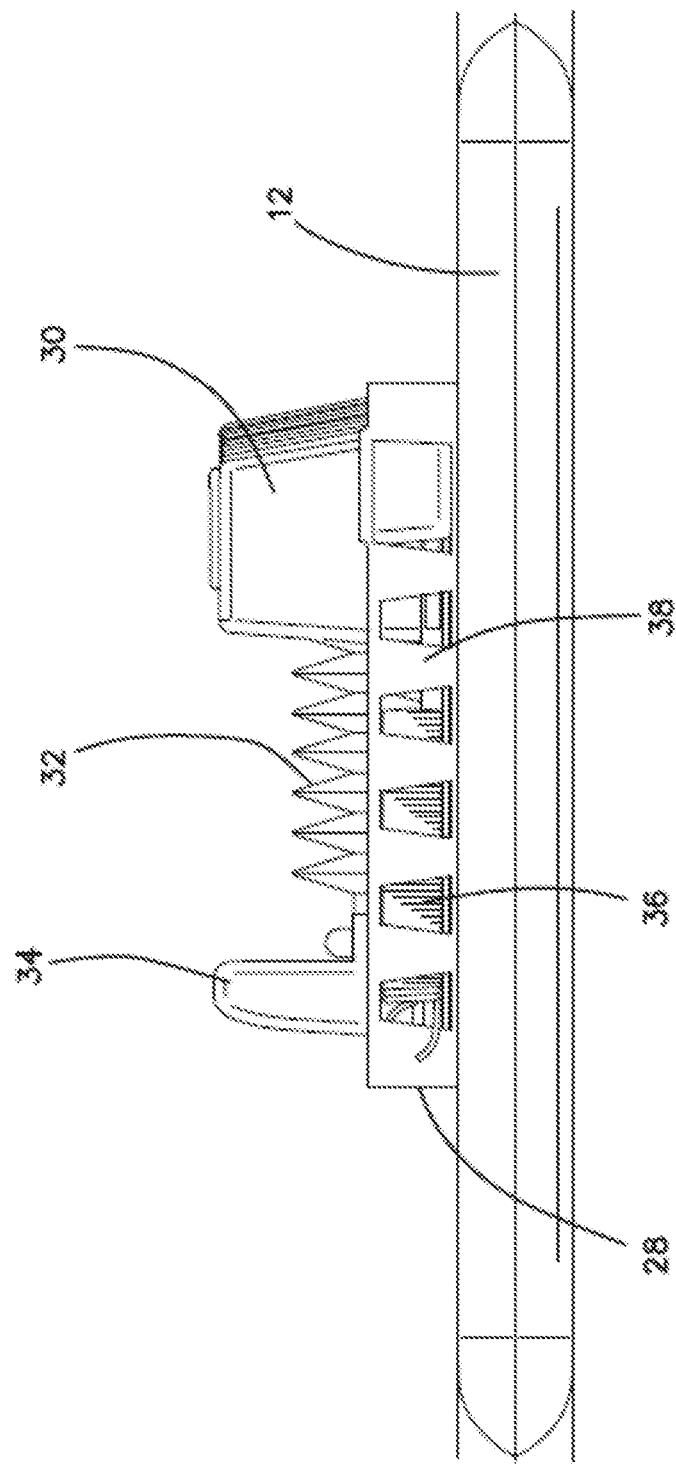
FIG. 7 is a side elevational view of the vacuum hand pump seen in FIG. 3 when the hand pump is in an expanded configuration.
Figure 8:
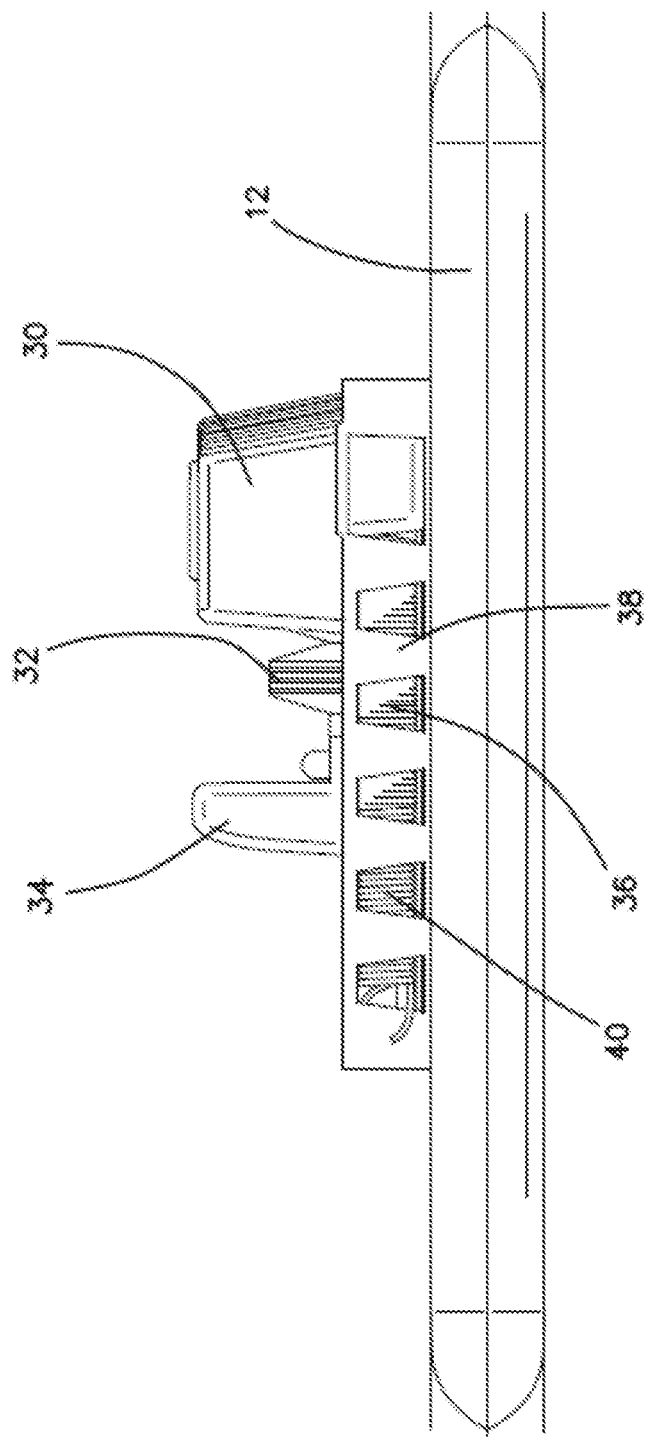
FIG. 8 is a side elevational view of the vacuum hand pump seen in FIG. 3 when the hand pump is in a compressed configuration.

After disposing the neck brace 10 around the neck of the patient and securing it in place, the user or medical professional operates the vacuum hand pump 26 by first placing his or her hand on top of the vacuum hand pump 26 seen in FIGS. 4 and 7 with the heel of his or her hand at or near the back of the housing 30 and fingers in front of the plunger 34. The user then compresses the vacuum hand pump 26 by squeezing the plunger 34 and bringing it back towards the stationary housing 30. As the user squeezes the plunger 34, the bellows 32 are compressed which drives air within the internal chamber 44 out of the housing 30 through the housing valve 42 in the direction of the arrows seen in FIG. 9. Specifically, air is driven towards the diaphragm 50 which lifts the outer circumference of the diaphragm 50 upward and off of the valve seat 48 and allowing the air to exit the housing 30. After the air pressure is equalized between the ambient environment and the internal chamber 44, the diaphragm 50 returns to its original position on the valve seat 48, thus preventing any air from reentering the internal chamber 44 of the housing 30. As the movement of the plunger 34 compresses the bellows 32, the shuttles 36 on either side of the vacuum hand pump 26 move through their respective tracks 38 and stretch each of the respective tension springs 40 coupled to each shuttle as seen in FIGS. 5 and 8.

After the bellows 32 has been fully compressed and the air driven from the internal chamber 44 of the housing 30, the user releases his or her grip on the plunger 34. The tension springs 40 then begin to compress and draw the plunger 34 away from the housing 30, thus expanding the bellows 32. The expanding bellows 32 in turn then draws air out of the body 12 of the neck brace 10 through the body valve 46 and into the internal chamber 44 of the housing 30. Once air has entered the internal chamber 44, the body valve 46 prevents its reentry back into the body 12 as is known in the art.

With air now back in the internal chamber 44 of the housing 30, the user once again may repeat the pumping process by compressing the plunger 34 and driving the air out of the housing 30 and into the ambient environment through the housing valve 42. It is in this manner that air is quickly and efficiently removed from the body 12 of the neck brace 10. With each subsequent stroke of the vacuum hand pump 26, a higher and higher vacuum is created within the body 12 which in turn removes air from the plurality of micro beads disposed within the body 12 which collapses under ambient exterior air pressure and presses the beads closer and closer together, thus making the body 12 more rigid and conforming the contours of body 12 to the shape of the patient's neck and shoulder region. The user continues to operate the vacuum hand pump 26 until the neck brace 10 is sufficiently rigidly set about the patient's neck and effectively immobilizes the patient's neck. With the neck brace 10 firmly in position, the patient may be moved as needed to receive further treatment without fear of further aggravating the patient's injuries.

To remove the neck brace 10 from the patient, the user opens a release valve 52 disposed on the back surface of the body 12 as seen in FIG. 2. The release valve 52 is a one-way valve known in the art which allows air to rush into the evacuated interior of body 12 previously pumped out by the vacuum hand pump 26. The reinserted air inflates or expands the neck brace 10 and relaxes the body 12. When the body 12 has sufficiently softened and has regained a certain amount of flexibility, the user may uncouple the ends of the body 12 from each other as disclosed above, unfold body 12 and remove the neck brace 10 from neck and shoulder region of the patient. While FIG. 2 shows the release valve 52 as being substantially disposed in a corner on the back surface of the body 12, it is to be expressly understood that this is for illustrative purposes only and that the release valve 52 may in fact be located anywhere on the front or back surface of the body 12 without significantly departing from the original intent and purpose of the current invention.

Figure 10:
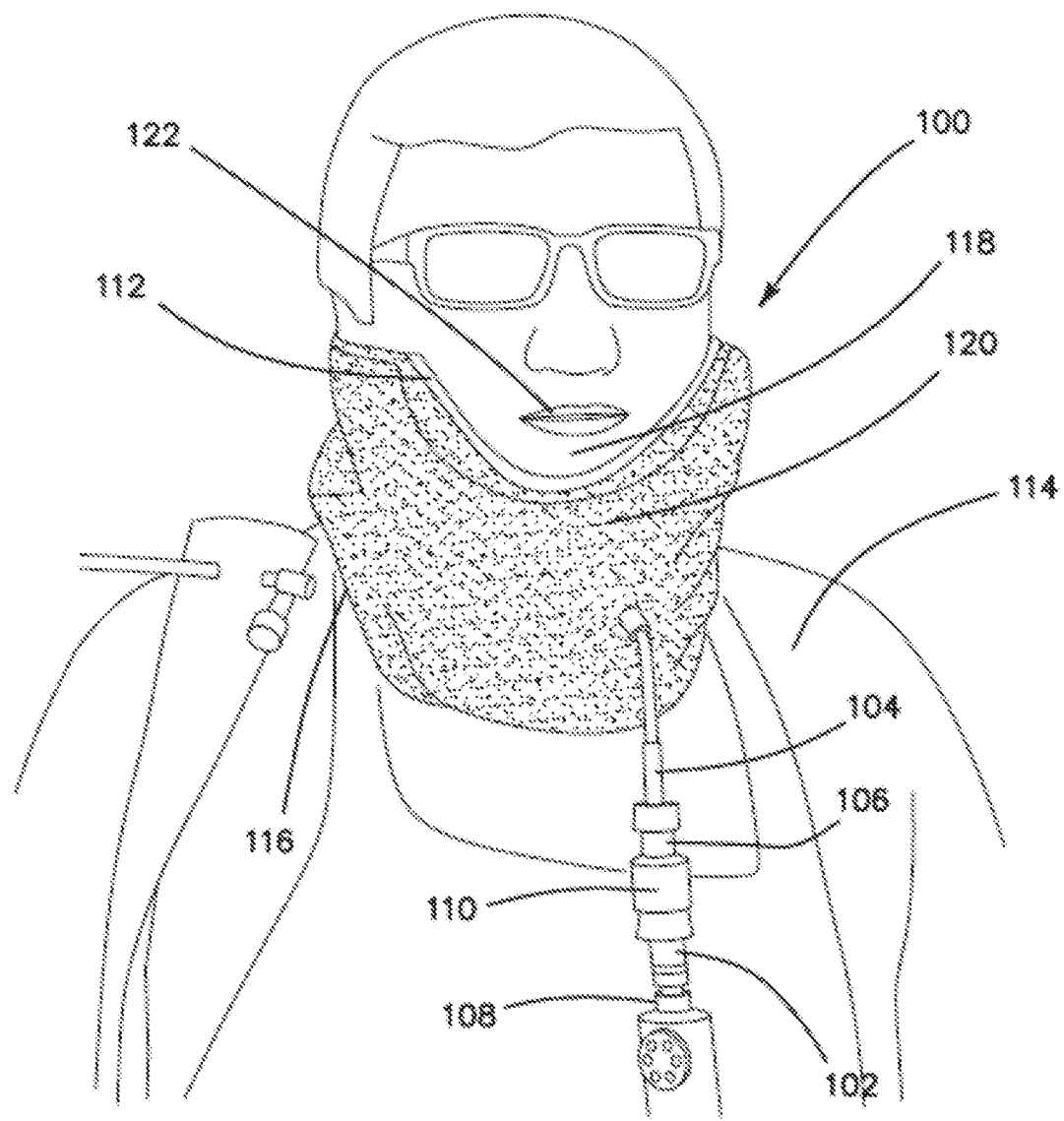
FIG. 10 is a frontal view of an alternative embodiment of the neck brace when disposed about the neck and chin of a patient.
Figure 11:
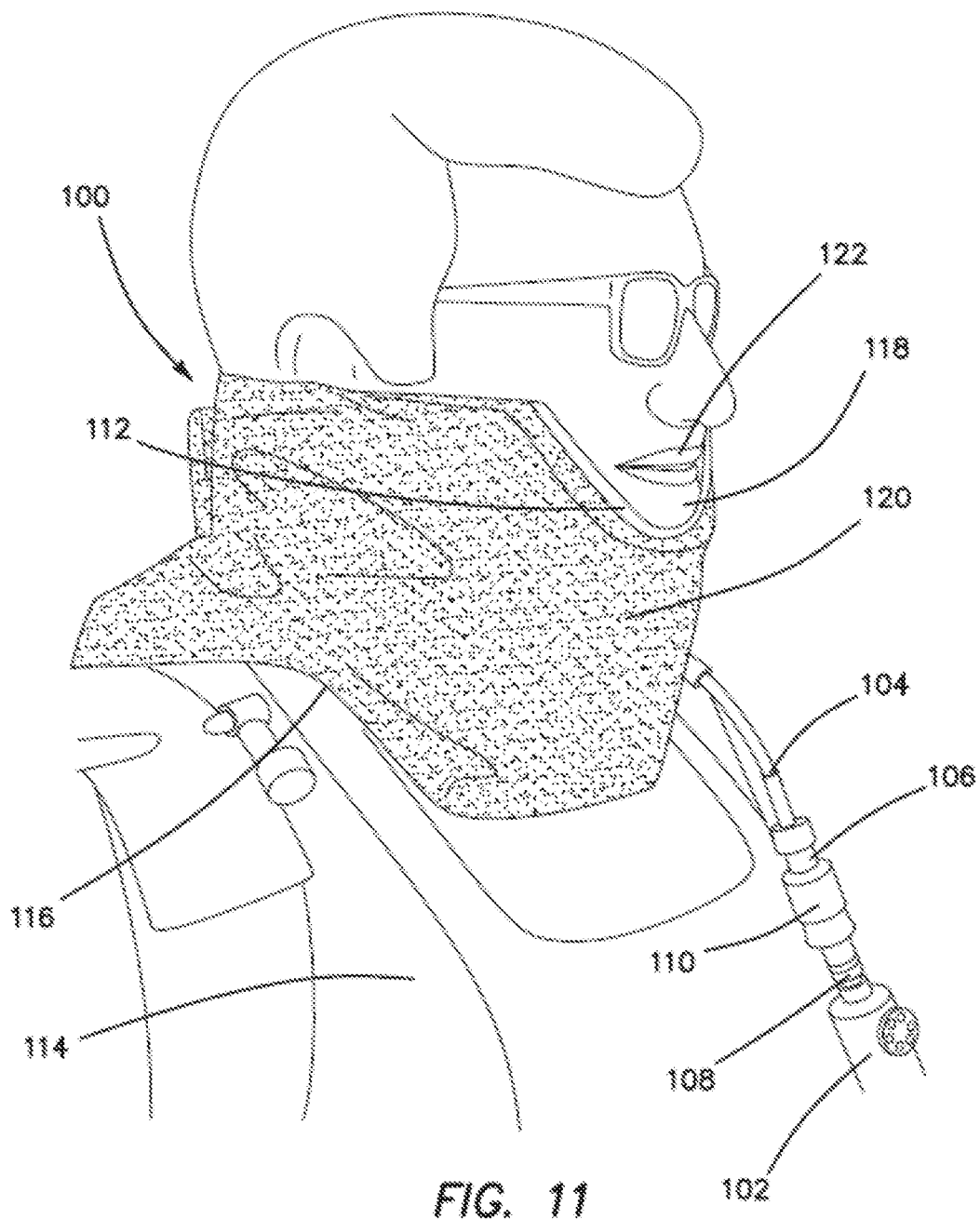
FIG. 11 is a perspective view of the alternative embodiment of the neck brace seen in FIG. 10.

In a separate embodiment, the hand pump 26 of the neck brace 10 may be replaced with a syringe pump 102 coupled to a neck brace 100 as seen in FIGS. 10 and 11. The syringe pump 102 is coupled to the neck brace 100 through a syringe aperture 104. The syringe aperture 104 is permanently coupled to an internal volume of the neck brace 100 at its proximal end. Disposed at a distal end of the syringe aperture 104 is a coupling portion 110 which is configured to accommodate a distal end of the syringe pump 102. The syringe aperture 104 further comprises a one-way directional valve 106 disposed within the coupling portion 110.

To use the syringe pump 102, a user wraps the neck brace 100 around the neck and shoulder region of a patient 114 as disclosed above. The syringe pump 102 is coupled to the syringe aperture 104 by inserting the distal end of the syringe pump 102 into the coupling portion 110 until the syringe pump 102 snaps or clicks into place via a friction fit or pressure fit as is known in the art. Alternatively, the neck brace 100 may be placed about the patient 114 in a pre-assembled state, namely with the syringe pump 102 already coupled to the syringe aperture 104. Once coupled, the user activates the syringe pump 102 by repeatedly manipulating a plunger disposed in the proximal end of the syringe pump 102 (not seen) as is known in the art. Specifically, as the plunger is drawn back, air from within the internal volume of the neck brace 100 is drawn out through the syringe aperture 104. As air exits the syringe aperture 104 it passes through the first one-way directional valve 106 and into the syringe pump 102. A second one-way directional valve 108 disposed within the syringe pump 102 directs air which has been drawn from the neck brace 100 into the ambient environment. The user then pushes the plunger of the syringe pump 102 back in the distal direction, the first and second one-way directional valves 106, 108 preventing air from flowing back into the neck brace 100 as is well known in the art. The user continues to manipulate the syringe pump 102 further drawing out air from the neck brace 100 and further contracting the neck brace 100 about the neck and shoulders of the patient 114 and creating a rigid neck brace as seen in FIGS. 10 and 11. Once the neck brace 100 has reached a sufficient level a rigidity, the user may stop manipulating the syringe pump 102 and let the syringe pump 102 hang down from the neck brace 100 in front of the patient 114. Alternatively, the user may detach the syringe pump 102 from the neck brace 100 by releasing the syringe pump 102 from the coupling portion 110 of the syringe aperture 104.

Greater functional detail of the neck brace 100 may also be had from FIGS. 10 and 11. Specifically, the neck brace comprises a plurality of shoulder cutouts 116 and a face cutout 112 which are sized and shaped within the neck brace 100 at the appropriate locations so that when the neck brace 100 is applied to the patient's 114 neck region, the face cutout 112 appropriately accommodates the jaw and chin of the patient while the shoulder cutouts 116 accommodate the shoulders and upper chest region of the patient 114. The face cutout 112 is a substantially half-moon shape cutout or aperture defined within a body portion 120 of the neck brace 100. As best seen in FIG. 11, the face cutout 112 is configured or defined to leave the nose and mouth 122 of the patient 114 open to the ambient environment while encompassing or enclosing the jaw and chin 188 of the patient 114 within the neck brace 100 when the neck brace 100 is wrapped about the patient 144 as disclosed above. Unlike prior neck braces, the neck brace 100 seen in FIGS. 10 and 11 explicitly allows for the disposition of the chin 118 within the neck brace 100 itself, thus dramatically increasing the overall comfort for the patient 114 wearing the neck brace 100 while still maintaining a sufficient level of immobilization required for effective medical treatment. Specifically, as is discussed above in relation to the previous embodiment, the neck brace 100 is placed or wrapped around the neck and chin 118 of the patient 114 while the body 120 of the neck brace 100 is in a soft or pliable state. With the patient's chin 188 still within the enclosed space formed by the applied neck brace 100, the user activates the neck brace 100 by removing air from within the neck brace 100 as disclosed above, thus contracting the neck brace 100 and forming a rigid three dimensional structure about the patient's neck and chin 118. Because the neck brace 100 contracts and forms to the specific contours of the patient's neck, shoulders, jaw, and chin 118, the patient 114 or the user do not need to remove the patient's chin 118 from within the enclosed space of the neck brace 100. Instead, the neck brace 100 forms a rigid structure which not only limits the relative movement of the patient's neck, but also prevents the patient's chin 118 from any undesired relative movement as well. In other words, as the user is wrapping the neck brace 100 about the patient 114, a comfortable and relaxed fit for the patient 114 is achieved since the neck brace 100 is initially soft and extremely pliable and does not place the patient in the discomfort of a near traction like state normally associated with neck braces or collars. The comfortable fit achieved by the neck brace 100 is then maintained upon its activation since the contracting movement and increasing rigidity of the neck brace 100 does not alter the position of the chin 118 of the patient 114 but rather "locks" it into an immobilized position.

An alternative embodiment of the invention may be seen in FIGS. 12A-17 where the neck brace is denoted generally as reference numeral 200. FIG. 12A shows a frontal view of the neck brace 200 which comprises a front panel 202, a back panel 218, and internal volume defined there between. Both the front panel 202 and the back panel 218 are substantially rectangular in shape with the exception of a neck contour 204 and a plurality of shoulder contours 206 defined within its overall structural form. The neck contour 204 and shoulder contours 16 are substantially "U" or "V" shaped definitions within the neck brace 200 that are defined along an upper edge 208 and a lower edge 210 of the front panel 202, respectively. When the neck brace 200 is applied to a patient's neck region as is described in further detail below, the neck contour 204 appropriately accommodates the jaw and head of the patient while the shoulder contours 206 accommodate each of the shoulders and the chest region of the patient as is known in the art. The neck brace 200 itself is comprised of soft, expandable fabric or other flexible material and is filled with a plurality of foam micro beads known in the art.

The neck brace 200 further comprises a strip 212 joined to a lateral edge of the front panel 202. Unlike the remaining portions of the neck brace 200, the strip 212 is not filled with a plurality of foam micro beads, thus allowing the strip 212 to remain flexible regardless of the state of rigidity of the remaining portions of the neck brace 200. The reverse side of the strip 212 seen in FIG. 12B comprises a first coupling portion 214 used to join the opposing ends of the neck brace 200 together when the neck brace 200 is placed around the neck of the injured patient. The first coupling portion 214 preferably comprises a hook and latch fabric pad, however other means such as adhesive surfaces or other mechanical means for coupling may be used so that when the neck brace 200 is placed on the patient, the strip 212 is brought around to the opposing end of the front panel 202 where a second coupling portion 220 is disposed. The medical professional secures the neck brace 200 in place by aligning the first coupling portion 214 on the back surface of the strip 212 with the second coupling portion 220 disposed on the opposing lateral edge of the front panel 202. The first coupling portion 214 and the second coupling portion 220 are brought together relative to one another according to the width or circumference of the patient's neck and shoulder region. In instances where the patient has a relatively small chest and shoulder region, for example when the patient is a child, the neck brace 200 may be further tightened by bringing a supplemental coupling portion 216 disposed on the back panel 218 of the neck brace 200 seen in FIG. 12B into contact with the second coupling portion 220. To release the neck brace 200, the first coupling portion 214 or the supplemental coupling portion 216 is pulled away or disengaged from the second coupling portion 220 thus releasing the lateral ends of the front panel 202 from each other. With the opposing ends of the front panel 202 separated, the neck brace 200 may be removed from the neck and shoulder region of the patient.

Figure 12C:
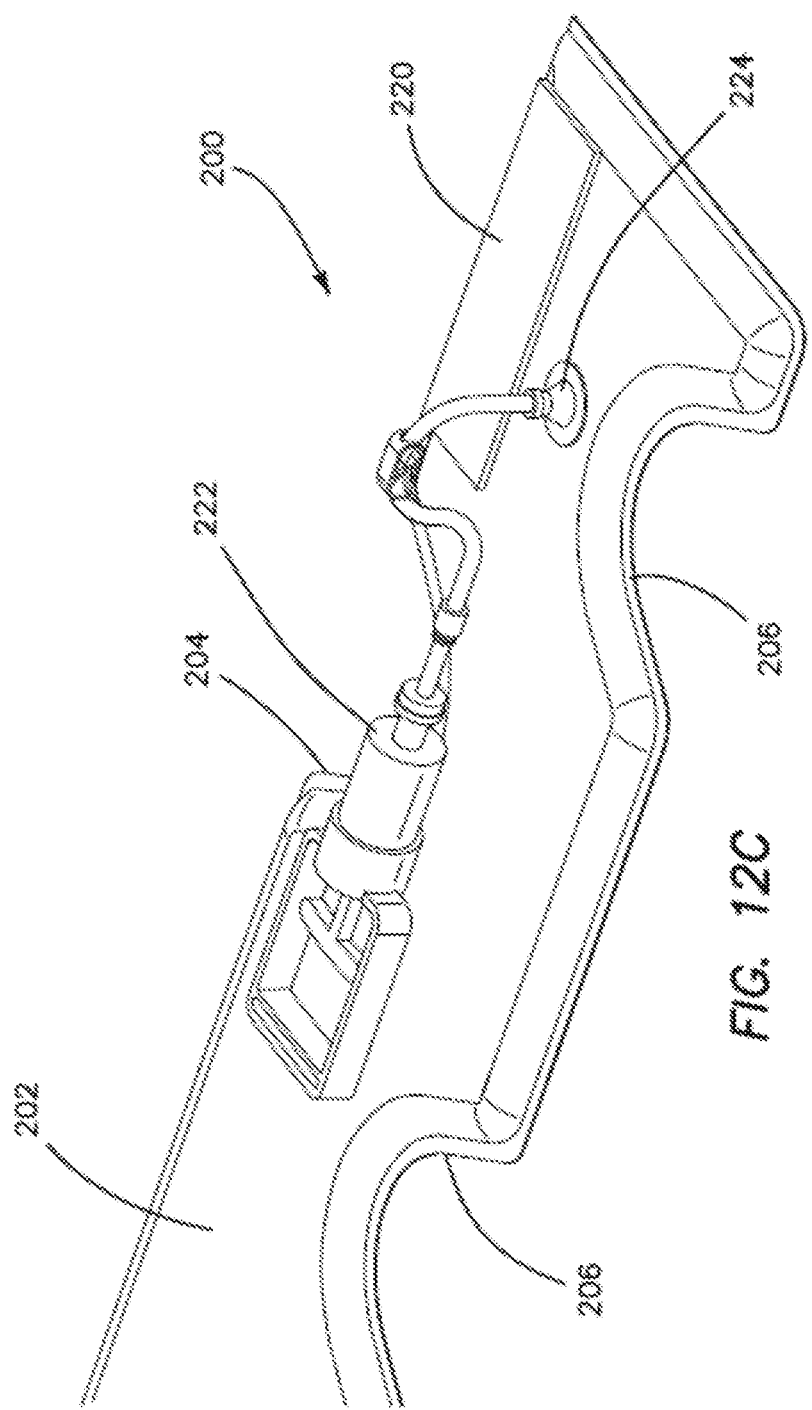
FIG. 12C is a magnified perspective view of the neck brace seen in FIG. 12A.
Figure 13:
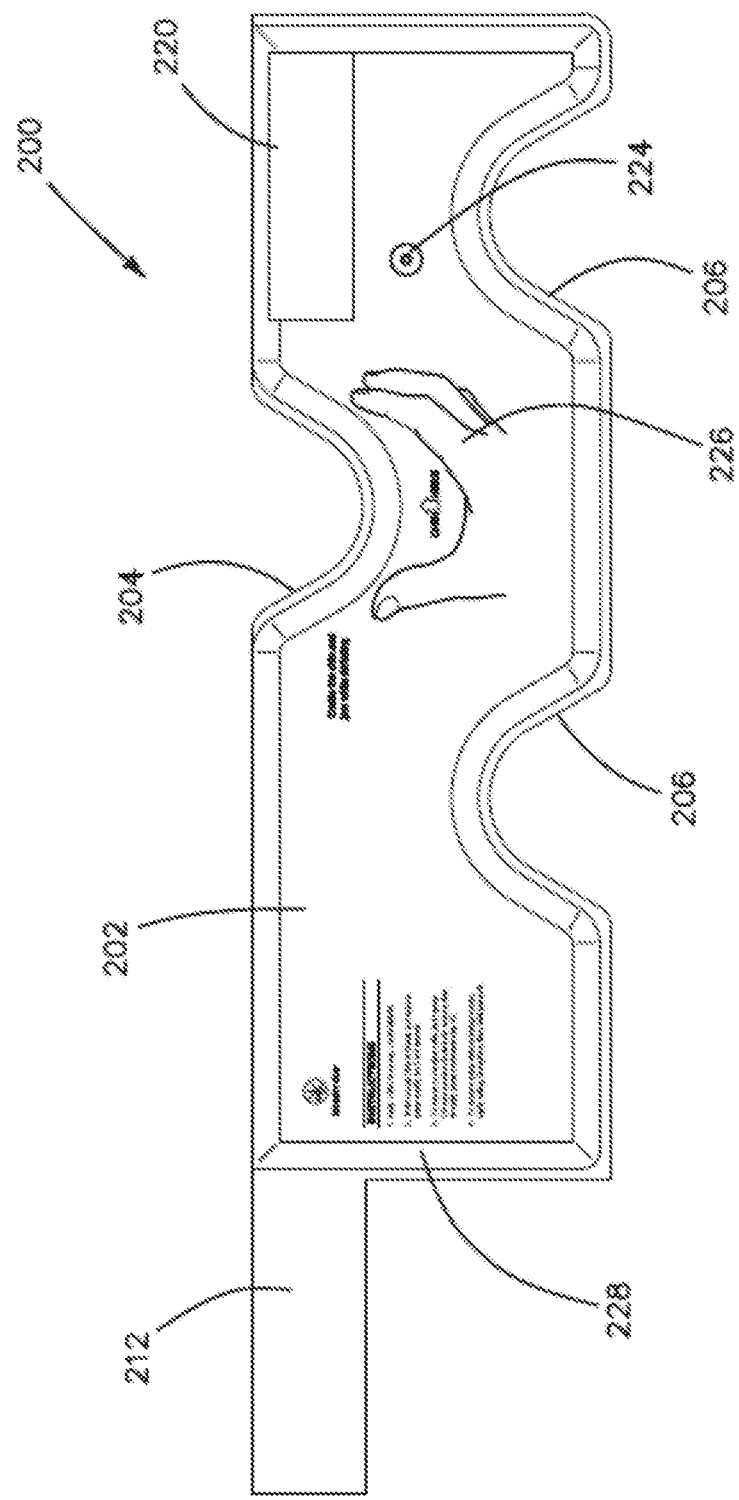
FIG. 13 is a top down perspective view of the neck brace seen in FIG. 12A after the detachable pump assembly has been removed.

As also seen in FIGS. 12A-12C, the neck brace 200 further comprises a detachable or removable single hand vacuum pump assembly 222. The detachable pump assembly 222 is removably coupled to an input valve 224 which is disposed within the front panel 202, preferably at a position within the front panel 202 that is beneath the second coupling portion 220 as seen in FIG. 12A and in FIG. 13 where the detachable hand pump assembly 222 has been removed. As also seen in FIG. 13, the front panel 202 may further comprise graphics 226 or text 228 printed on its outward surface which preferably directs or shows the medical professional how to properly apply the neck brace 200 to a patient.

Figure 14A:
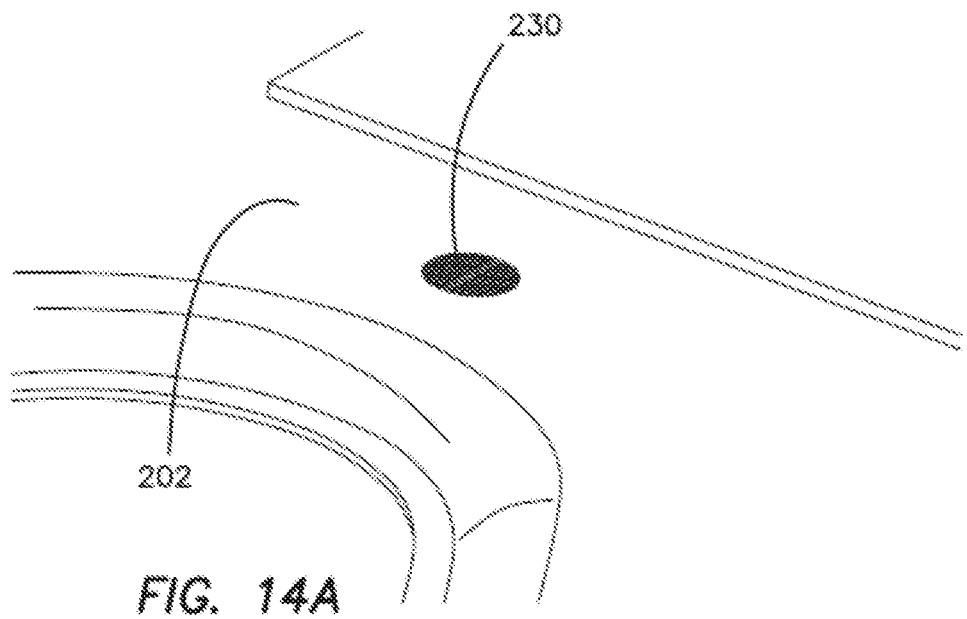
FIG. 14A is a magnified perspective view of an inlet defined within the neck brace, the inlet comprising a filter screen.
Figure 14B:
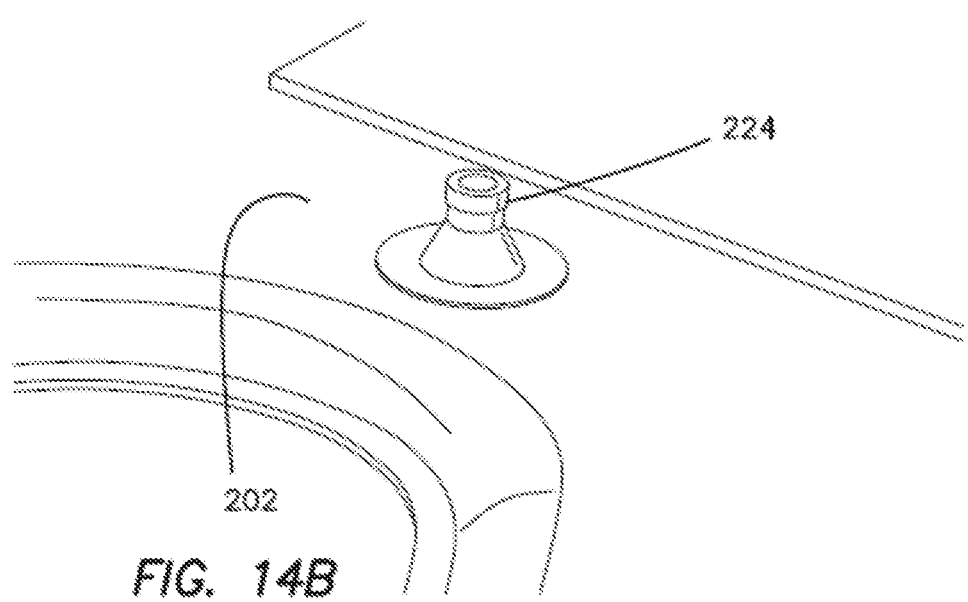
FIG. 14B is a magnified perspective view of the inlet seen in FIG. 14A with an input valve disposed over the filter screen.
Figure 14C:
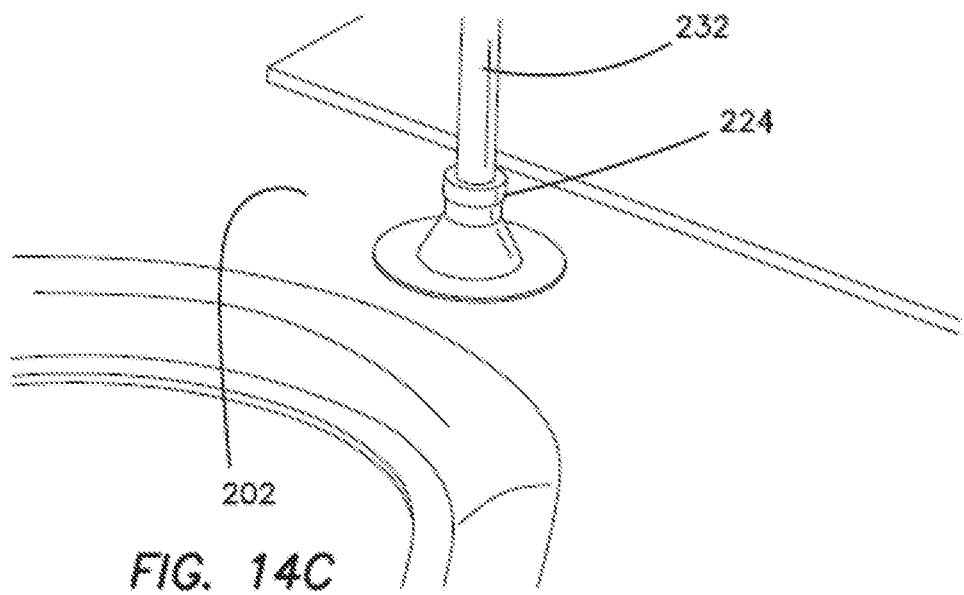
FIG. 14C is a magnified perspective view of the input valve seen in FIG. 14B after a vacuum line has been coupled to the input valve.

Further detail of the input valve 224 may be had by turning to FIGS. 14A-14C. FIG. 14A shows the front panel 202 of the neck brace 200 when the input valve removed and showing a filter mesh or screen 230 defined within the surface of the front panel 202. The input valve 224 is then coupled or incorporated into the front panel 202 directly over the filter screen 230 as seen in FIG. 14B. A distal end of a vacuum line 232 is then in turn coupled to the input valve 224 as shown in FIG. 14C. When the detachable pump assembly 222 is in use, the filter screen 230 allows air trapped within the neck brace 200 to pass through the front panel 202 and into the vacuum line 232 through the input valve 224 while simultaneously preventing any of the plurality of foam micro beads from escaping the neck brace 200 and thus possibly jamming or blocking the input valve 224 or vacuum line 232.

Figure 15:
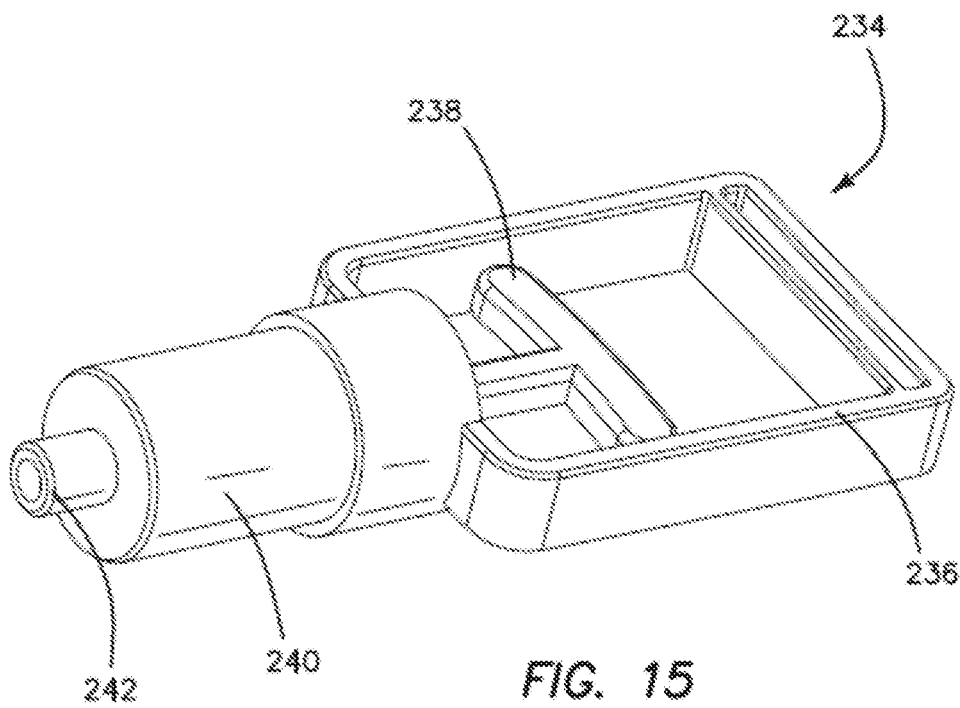
FIG. 15 is a perspective view of the detachable pump assembly.
Figure 16:
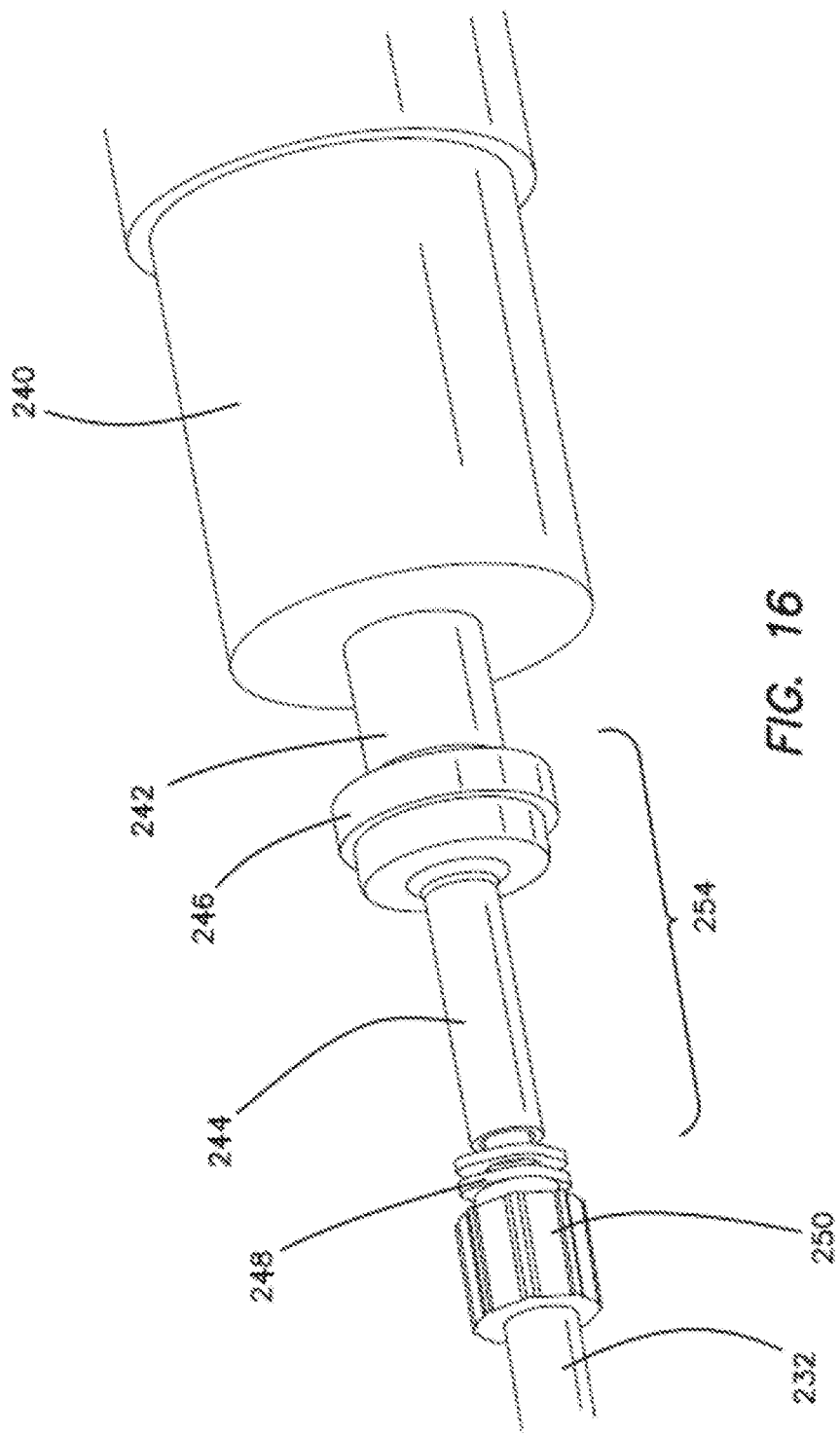
FIG. 16 is a magnified view of the coupling between the detachable pump assembly and the vacuum line coupled to the neck brace.
Figure 17:
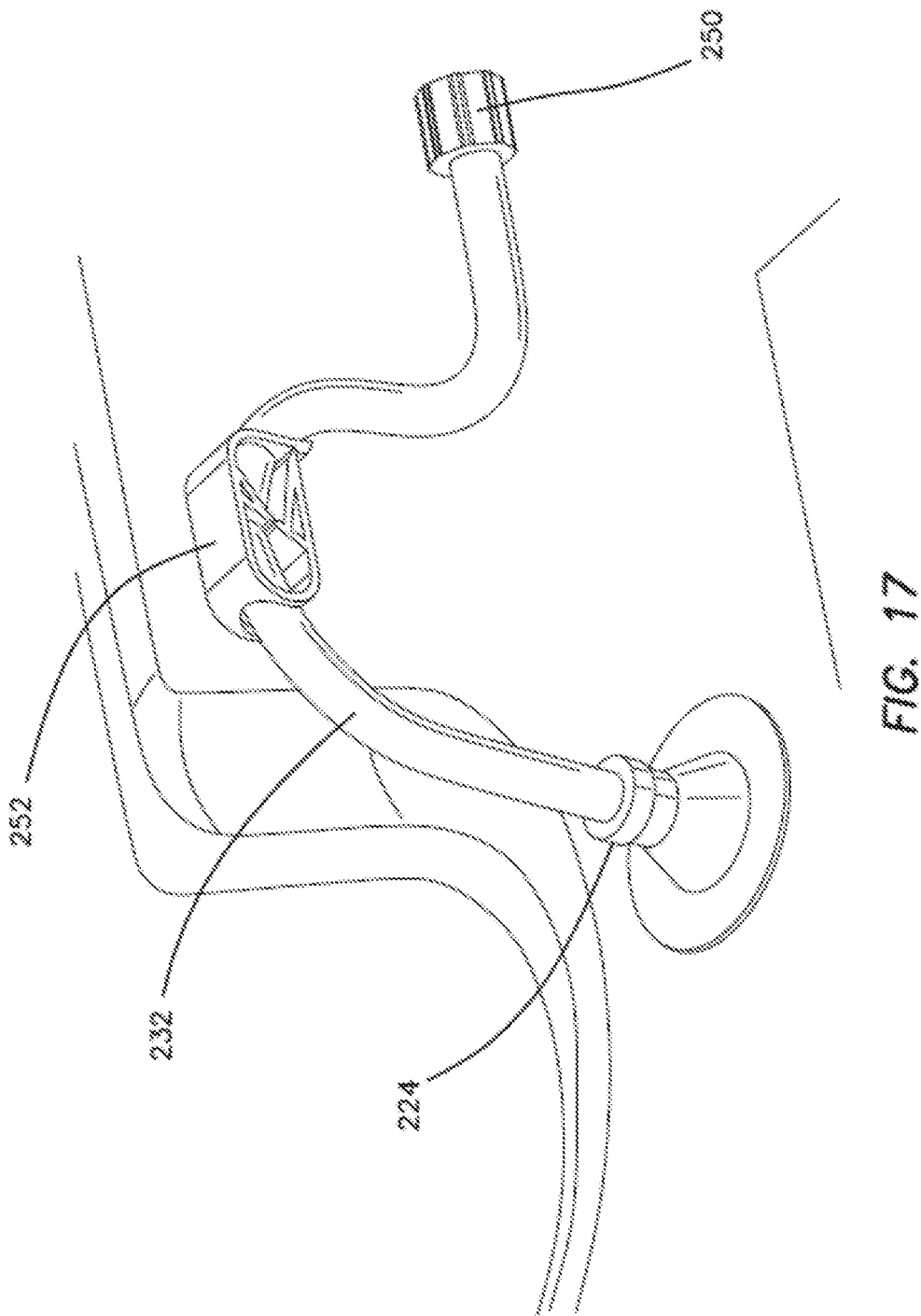
FIG. 17 is a magnified view of the vacuum line coupled to the neck, the vacuum line comprising a hose clamp.
Figure 18:
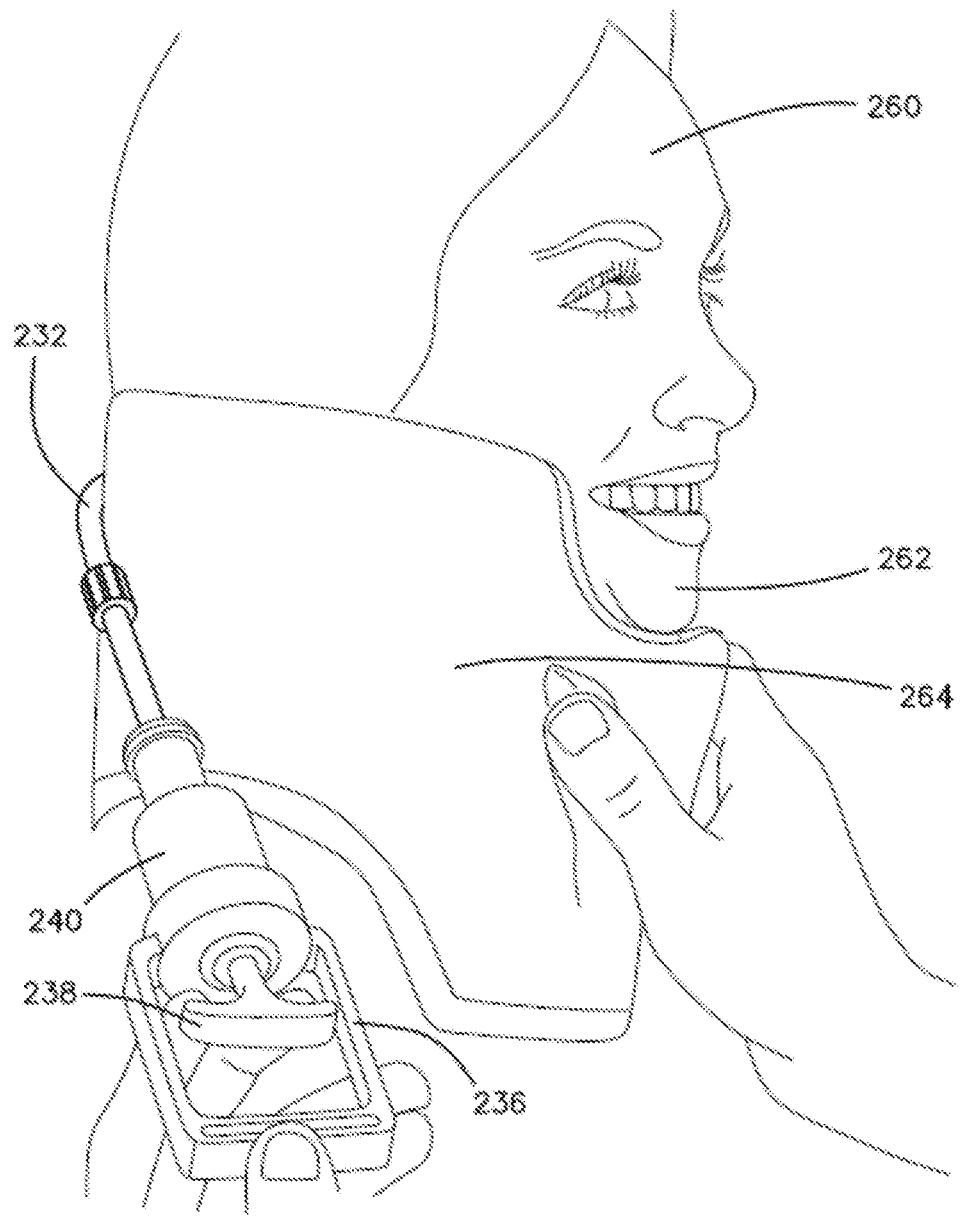
FIG. 18 is a view of the neck brace forming a patient-specific mold about the neck and shoulder region of the patient.

Greater detail of the detachable pump assembly 222 may be had from FIGS. 15-17. FIG. 15 is a detailed view of the pump unit 234 which comprises a handle portion 236, a plunger 238, a chamber 240, and a nozzle 242. Specifically, the handle 236 is preferably rectangular in shape and coupled to the chamber 240. The plunger 238 is disposed within an internal portion of the chamber 240 along with a spring as is known in the art so that when the plunger 238 is pulled in the distal direction away from the chamber 240, air is drawn in from the nozzle 242 disposed at the opposing end of the chamber 240. The handle 236 and plunger 238 are configured or arranged so that the distal edge of the handle 236 may be pressed against the medical professional's thumb or palm while their fingers are wrapped or hooked around the plunger 238. The medical professional actuates the pump unit 234 by pulling the plunger 238 towards their palm, thus expanding the internal volume within the chamber 240 and drawing air in from the nozzle 242. The medical professional then relaxes their grip, allowing a spring within the chamber 240 to expand and push the plunger 238 back towards the chamber 240.

FIG. 16 shows how the pump unit 234 may be coupled to the vacuum line 232. Coupled between the nozzle 242 of the pump unit 234 and the vacuum line 232 is a coupling sub assembly 254 which comprises a collar 246 bonded to the nozzle 242, a flexible connecting line 244 bonded to the collar 246, and a female luer lug style to barb 248 which is in turn bonded to the distal end of the flexible connecting line 244. The collar 246 comprises a one-way valve that is configured to allow air to flow in one direction so that when the plunger 238 is returned to its original starting position, air is not pushed back out of the nozzle 242 and subsequently into the neck brace 200. The vacuum line 232 further comprises a male luer integral lock ring 250 disposed at its distal tip as seen in FIG. 17. To connect the pump assembly 222, the medical professional couples the female luer lug 248 to the male luer lock 250 as is known in the art. To detach the pump assembly 222 from the neck brace 200, the medical professional simply decouples the female luer lug 248 from the male luer lock 250.

As also seen in FIG. 17, a hose clamp 252 is coupled to the vacuum line 232. After actuating the pump assembly 222 and removing the air from within the neck brace 200, the hose clamp 252 may be actuated so that no air reenters the neck brace 200, thus allowing the medical professional to decouple the pump assembly 222 via the female luer lug 248 and male luer lock 250. To re-inflate the neck brace 200, the medical professional can open the hose clamp 252, thus allowing ambient air to rush into the neck brace 200 through the vacuum line 232 and input valve 224. Alternatively, the medical professional may instead open a release valve that is structural distinct from the vacuum line and which is disposed within the front panel 202 of the neck brace.

To use the neck brace 200, the neck brace 200 is first placed or wrapped around the neck and chin 262 of a patient 260 while the neck brace 200 itself is in a soft or pliable state. With the patient's chin 262 still within the enclosed space formed by the applied neck brace 200, the user activates the detachable pump assembly 222 by squeezing the plunger 238 and handle 236 for four to six seconds as disclosed above, thus removing air from the neck brace 200 and contracting it to form a rigid three dimensional structure or mold 264 about the patient's neck and chin 262. Because the neck brace 200 contracts and molds to the specific contours of the patient's neck, shoulders, jaw, and chin 262, the patient 260 or the medical professional do not need to remove the patient's chin 262 from within the enclosed space of the neck brace 200. Instead, the neck brace 200 forms a rigid structure which not only limits the relative movement of the patient's neck, but also prevents the patient's chin 262 from any undesired relative movement as well. The comfortable fit achieved by the neck brace 200 is then maintained upon its activation since the contracting movement and increasing rigidity of the neck brace 200 does not alter the position of the chin 262 of the patient 260 but rather "locks" it into an immobilized position.

Additionally, because the neck brace 200 is initially soft and extremely pliable, it may be placed on the patient 260 in the same condition the medical professional finds the patient in, thus negating the need to first put the patient in traction or otherwise distract the patient's neck. For example, many conventional cervical collars require the patient's head and chin to first be lifted upwards in order for the permanently rigid collar or brace to be wrapped about the patient's neck. If the patient has suffered an unknown neck injury however, the last thing a first responder should do is to distract the patient's neck and possibly exacerbate or further worsen the patient's injury. The neck brace 200 of the current invention is instead applied to the neck region of the patient while it is in a pliable or malleable state, therefore the specific relative position of the injured patient's head, chin, or neck does not need to be altered or distracted in order to place the neck brace 200 into its proper position. Furthermore, because the neck brace 200 forms a mold 264 about the patient's neck and shoulders, the neck brace 200 may be placed around the patient's neck region regardless of the patient's clothing or hair which typically impedes or blocks the placement of a traditional permanently rigid cervical collar or brace. In short, the current neck brace 200 does not place the patient in the discomfort of a near traction like state normally associated with neck braces or collars and instead forms a patient-specific mold 264 which prevents further distraction of the patient's neck.

Furthermore because the current neck brace 200 forms a patient-specific mold 264 and does not need to be applied directly to the surface of patient's neck in order to immobilize the patient's movement, the current neck brace 200 does not restrict or alter the patient's blood flow while the neck brace 200 is in use. As is well known, a number of veins are disposed within the neck region of the patient including the internal jugular vein. When a traditional permanently rigid brace or collar is placed about the patient's neck and then tightened, this can press upon the internal veins of the patient and detrimentally effect the patient's venous return. Slowing the patient's venous return can cause discomfort to the patient at a minimum, and depending upon the nature and extent of the patient's condition or injury, a slowing or restriction of the venous return can dramatically worsen the patient's condition by restricting blood flow back to the heart.

When the neck brace 200 is to be removed from the patient, the medical professional may decouple the pump assembly 222 from the male luer lock 250 disposed on the vacuum line 232 and then disengage the hose clamp 252, thus allowing ambient air to reenter the internal volume of the neck brace 200. As air enters the neck brace 200, its rigidity decreases and the neck brace 200 once again regains its malleable, deformable shape. The medical professional may then decouple the strip 212 from the second coupling portion 220 as described above and then remove the neck brace 200 from around the neck of the patient.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A customizable neck brace comprising:
   a front panel;
   a back panel, wherein an internal volume is defined between the front panel and the back panel;

a strip coupled to the front panel, the strip comprising a first coupling portion disposed on at least one surface of the strip;
a second coupling portion disposed on the front panel;
a plurality of loosely compressible particles disposed in the internal volume;
a detachable pump assembly removably coupled to the front panel; and
a neck contour defined in the front panel and back panel, where the detachable pump assembly comprises:
a chamber;
a handle coupled to a first end of the chamber;
a plunger disposed within an internal portion of the chamber; and
a nozzle disposed within a second end of the chamber.

2. The neck brace of claim 1 where the detachable pump assembly further comprises:
a vacuum line coupled to an input valve disposed in the front panel at a first end;
a male luer lock coupled to a second end of the vacuum line.

3. The neck brace of claim 2 further comprising a hose clamp coupled to the vacuum line.

4. The neck brace of claim 1 where the front panel further comprises an input valve fluidly communicated to the internal volume.

5. The neck brace of claim 4 where the input valve further comprises a filter screen disposed between the internal volume an internal portion of the input valve.

6. The neck brace of claim 1 where the detachable pump assembly further comprises a collar coupled to the nozzle and a female luer lug which is coupled to the nozzle via a flexible connecting line.

7. The neck brace of claim 1 further comprising a supplemental coupling portion disposed on the back panel.

8. The neck brace of claim 1 further comprising a plurality of shoulder contours defined in the front panel and the back panel.

9. The neck brace of claim 1 wherein the front panel and the back panel cooperate to form a patient-specific mold around the neck of and chin of a patient after the detachable pump assembly has been actuated.

10. A method for forming an immobilizing patient-specific mold comprising:
wrapping a neck brace around the neck and chin of a patient, the neck brace comprising a front panel and a back panel and having an interior volume defined therebetween, where the internal volume is filled with a plurality of compressible particles;
actuating a detachable pump assembly removably coupled to the front panel of the neck brace; and
removing air from the internal volume of the neck brace to compress the neck brace and forming a unique rigid mold about the neck and chin of the patient,
where actuating the detachable pump assembly comprises:
removably coupling a pump unit to a vacuum line communicated to the internal volume of the neck brace;
actuating a plunger disposed within a chamber of the pump unit; and
removing air from the internal volume of the neck brace through the vacuum line.

11. The method of claim 10 where removing air from the internal volume of the neck brace through the vacuum line further comprises preventing the plurality of compressible particles within the internal volume from entering the vacuum line with a filter screen.

12. The method of claim 10 where removably coupling a pump unit to a vacuum line communicated to the internal volume of the neck brace comprises coupling a female luer lug disposed on the pump unit to a male luer lock disposed on the vacuum line.

13. The method of claim 10 where forming a unique rigid mold about the neck and chin of the patient comprises accommodating the chin of the patient in an immobilized position within the unique rigid mold.

14. The method of claim 10 where forming a unique rigid mold about the neck and chin of the patient further comprises preventing restriction of the venous blood flow return of the patient.

15. A method for preventing the distraction of the neck of a patient when immobilizing the patient's neck comprising:
disposing a neck brace about the neck of a patient while the neck of the patient is in an injured position; and
actuating the neck brace to form a unique rigid mold about the injured region of the patient's neck,
wherein the formed unique rigid mold is configured to maintain the neck of the patient within its original injured position for the duration that the neck brace is disposed about the neck of the patient, and
where actuating the neck brace to form a unique rigid mold about the injured region of the patient's neck comprises:
removably coupling a pump unit to a vacuum line communicated to an internal volume of the neck brace;
actuating a plunger disposed within a chamber of the pump unit; and
removing air from the internal volume of the neck brace through the vacuum line.

16. The method of claim 15 where actuating the neck brace to form a unique rigid mold about the injured region of the patient's neck comprises compressing the neck brace to fit the specific contours of the patient's neck and chin.

17. The method of claim 15 further comprising inflating the neck brace and removing the neck brace from the neck of the patient.

18. The method of claim 15 where disposing a neck brace about the neck of a patient while the neck of the patient is in an injured position comprises coupling a first coupling portion or a supplemental coupling portion disposed on a first surface of the neck brace to a second coupling portion disposed on a second surface of the neck brace.

\* \* \* \* \*